(12) United States Patent
Dziubak et al.

(10) Patent No.: US 10,080,492 B2
(45) Date of Patent: Sep. 25, 2018

(54) METHOD AND SYSTEM FOR MOTION ARTEFACTS REMOVAL IN OPTICAL COHERENCE TOMOGRAPHY

(71) Applicant: CANON KABUSHIKI KAISHA, Tokyo (JP)

(72) Inventors: Tomasz Dziubak, Torun (PL); Marek Rózanski, Torun (PL); Tomasz Bajraszewski, Glogowo (PL)

(73) Assignee: Canon Kabushiki Kaisha, Tokyo (JP)

( * ) Notice: Subject to any disclaimer, the term of this patent is extended or adjusted under 35 U.S.C. 154(b) by 10 days.

(21) Appl. No.: 15/453,803

(22) Filed: Mar. 8, 2017

(65) Prior Publication Data
US 2017/0258317 A1    Sep. 14, 2017

(30) Foreign Application Priority Data
Mar. 10, 2016 (EP) .................................. 16159636

(51) Int. Cl.
*A61B 3/14* (2006.01)
*A61B 3/00* (2006.01)
(Continued)

(52) U.S. Cl.
CPC ............ *A61B 3/0025* (2013.01); *A61B 3/102* (2013.01); *A61B 3/1241* (2013.01)

(58) Field of Classification Search
CPC ...... A61B 3/0025; A61B 3/1241; A61B 3/102
(Continued)

(56) References Cited

U.S. PATENT DOCUMENTS

| 7,768,652 B2* | 8/2010 | Everett ............... A61B 5/0059 356/497 |
| 8,223,143 B2* | 7/2012 | Dastmalchi ............ A61B 3/102 345/418 |
| 2007/0291277 A1* | 12/2007 | Everett .................. A61B 3/102 356/497 |

FOREIGN PATENT DOCUMENTS

| JP | 2011-254959 | 12/2011 |
| JP | 2013-169309 | 9/2013 |

(Continued)

OTHER PUBLICATIONS

Tomasz Bajraszewski, et al.; "Three-dimensional in vivo imaging by spectral OCT"; Institute of Physics, Nicolaus Copernicus University, ul. Grudziadzka 5, 87-100 Torun, Poland; Coherence Domain Optical Methods and Optical Coherence Tomography in Biomedicine VIII, edited by Valery V. Tuchin, Joseph A. Izatt, James G. Fujimoto, Proc. of SPIE, vol. 5316; pp. 226-232.

*Primary Examiner* — Tuyen Tra
(74) *Attorney, Agent, or Firm* — Canon U.S.A., Inc. IP Division

(57) ABSTRACT

A method and system for compensating for motion artefacts in Optical Coherence Tomography is provided. A B-scan set includes a plurality of B-scan images acquired at least a position corresponding to a target position of a fundus of an eye. The plurality of B-scans within the B-scan set are aligned using a first alignment process and a second alignment process, where the second alignment process is performed on the B-scan images within the B-scan set aligned by the first alignment process. The first alignment process aligns the B-scan images within the B-scan set at a first resolution in at least an axial direction, and the second alignment process aligns the B-scan images within the B-scan set aligned in the first alignment process at a second (Continued)

resolution having a higher resolution than the first resolution in at least the axial direction.

13 Claims, 16 Drawing Sheets

(51) Int. Cl.
*A61B 3/10* (2006.01)
*A61B 3/12* (2006.01)
(58) Field of Classification Search
USPC .......................................... 351/200, 205, 206
See application file for complete search history.

(56) References Cited

FOREIGN PATENT DOCUMENTS

| | | |
|---|---|---|
| JP | 2014-140491 | 8/2014 |
| JP | 2015-131107 | 7/2015 |
| WO | 2006/077107 A1 | 7/2006 |
| WO | 2014103501 | 3/2014 |
| WO | 2015/120055 A1 | 8/2015 |

* cited by examiner

METHOD AND SYSTEM FOR MOTION ARTEFACTS REMOVAL IN OPTICAL COHERENCE TOMOGRAPHY

BACKGROUND OF THE INVENTION

Field of the Invention

The present invention relates to a method and a system for removing motion artefacts in Optical Coherence Tomography.

Description of the Related Art

Optical Coherence Tomography (OCT) is an established medical imaging technique that uses coherent light to capture tomographic images of a subject. In recent times, Angiography (OCTA) is developed as a desirable non-invasive imaging technique for generating volumetric angiography images of a fundus of an eye.

Non-patent literature 1 and non-patent literature 2 discuss a common method of OCTA image generation based on amplitude decorrelation algorithms that are applied to a number of images acquired from the same position of an eye. Any blood flow in the tissues (e.g. blood vessels (including capillaries)) causes a signal intensity variation, while other (stationary) tissues without any blood flow do not cause any intensity variation of the signal. Thus, the amplitude decorrelation processing detects the intensity variation and emphasizes the blood flowing (moving) within the fundus.

Although the number of images at the same position of an eye are taken in quick succession, movement of the eye between and/or during each image taking can still occur. Any movement of the eye between repeated images (B-scans) during OCTA examination can cause a significant increase of artefacts in the decorrelation signal (i.e. differences between the images). This is because the repeated images will be different from each other, and since the amplitude decorrelation algorithm detects and emphasizes differences in signal intensity regardless of the source of such changes, all changes including different positions of tissues other than blood vessels will be detected.

In order to perform OCT and OCTA a measurement scanning beam from an OCT apparatus is directed into one of the eyes of a patient. The patient's eye movements in relation to the scanning beam can be divided into two kinds, namely eye-induced movements and head-induced movements. Eye-induced movements are rapid and can significantly change the position of the retina against the scanning beam in a transverse direction. Head-induced movements, however, are not rapid and can be considered as a kind of drift caused by breathing, blood pulses, or the general condition of the patient. Head-induced movements may occur in a transverse direction (e.g. side-to-side with respect to the scanning beam) or a longitudinal direction (e.g. along the direction of the scanning beam).

Transverse head movement and longitudinal head movements have a different influence on the OCT tomogram. FIG. 1 shows these differences. Part A of FIG. 1 shows at the top a diagram indicating transverse head movement, and at the bottom the resultant tomogram. Part B shows at the top a diagram indicating longitudinal head movements, and at the bottom the resultant tomogram.

As FIG. 1 shows, transverse head movements (part A) produce a tilt of the retinal signal on the corresponding OCT tomogram. This is because movements in the XY plane influence the position of a pivot of the scanning beam, and cause a path length change along the X or Y axis. It can be seen that such transverse movement does not necessarily change the average position on the Z-axis (as shown). In the case of longitudinal head movements (part B), the average position on the Z-axis varies significantly, but the retinal signal tilt is relatively maintained. In a typical case, a combination of both types of head movement is present during OCT measurement.

Head-induced movements, although not rapid, may significantly degrade the OCTA image quality. This is due to the high sensitivity of the amplitude decorrelation based methods used to generate the motion contrast image (e.g. angiogram). It is well known that OCT structural images are disturbed by speckle noise in which the axial size of the speckles is comparable to the axial optical resolution of the OCT apparatus, and the transverse size of the speckles is given by the spot size of the scanning beam OCT apparatus at the object. In a high-resolution OCT apparatus, the axial resolution may be as low as 3 µm, while the transverse resolution is between approximately 15 to 25 µm and is limited mainly by the optical properties of the human eye. Hence, any phenomenon which can modify two tomograms in the Z-axis at the level of half the size of a speckle may cause a significant increase of the decorrelation signal.

For example, consider the case of an OCT apparatus that has an acquisition speed of 70,000 kHz, obtaining two images consisting of 300 A-scans each of which will be analysed for motion contrast. The time interval between obtaining the two images will be approximately 5 ms. Decorrelation will be significantly disturbed when a shift between the two images in the Z-axis is half of a speckle, i.e. ½ of 3 µm. Thus, a speed of eye movement that would significantly disturb the motion contrast image will be approximately 1.5 µm/5 ms=0.3 mm/s. Such eye movement could easily be achieved by processes such as breathing, or the inaccuracy of head fixation of a patient while performing the measurement.

FIG. 2 shows a 3×3 mm region of an in vivo OCTA projection map influenced by eye movements during the acquisition (measurement). Specifically the patient's eye movements are along the Z-axis, and the influence on the OCTA projection map can be clearly seen as (white) horizontal lines.

To obtain such an image, two mirrors (e.g. galvanometric driven mirrors) are required to manipulate a scanning beam in two transverse directions X and Y. For raster scan pattern, typically the X-mirror performs scanning along the X-axis to obtain a single B-scan and the Y-mirror shifts the beam to a new location along the Y-axis to collect the next B-scan. However, an angle can be applied to the scanning pattern meaning that the single B-scan is acquired by manipulating both the X and Y mirrors. Hence, hereinafter, a fast axis will be discussed as an axis given by direction of acquiring a single B-scan, and a slow axis will be discussed as an axis given by the direction of acquiring another B-scan or B-scan sets.

There are two known strategies or methods aimed at reducing the influence of eye movements on OCTA projection maps. These two methods of OCTA processing for a single B-scan set are illustrated in FIG. 3 as method A on left and method B on the right.

Method A will be described first. In step 1 the sets of B-scans are acquired. Depending on the OCTA technology used, each B-scan can be repeated several times (minimum once). After acquisition of the B-scans, the tomogram reconstruction process is applied to each B-scan (step 2).

In step 3 an alignment process is applied within a single set of B-scans independently for each set of B-scans. In other words, for a set of B-scans obtained at a particular slow-axis position (X or Y position) (B-scan set), the alignment process is applied for that set independently from any other B-scan set. The purpose of this step is to compensate for small displacements between the B-scans caused by eye motions during the acquisition.

In step 4, the angiograms are calculated for each pair of adjacent B-scans. In step 6 the final angiogram is calculated by, for example, a combination of the angiograms calculated in step 4 (e.g. by using maximum image projection, average or median or any other combination).

Method B differs from method A by omitting step 3 and including an additional step 5. Because step 3 is not present in method B, the angiograms are calculated for each pair of B-scans in step 4 regardless of whether the B-scans are corrupted, or influenced, by eye movements. However, method B includes the additional step 5, in which the angiograms corrupted by eye movement are removed. The final angiogram is calculated in step 6 as a combination of the remaining angiograms.

The main difference between method A and method B is the way of dealing with eye movements. Method A tries to compensate for eye movements in post-processing, whereas method B removes the angiograms influenced by eye movements. Method B was described in non-patent literature 1.

In method B, step 5 requires the determination of a threshold value which is applied to decide whether a tomogram is influenced by eye movements, and consequently, whether to delete the tomogram or not. This way it can efficiently remove artefacts caused by significant eye movements and can therefore reduce some strong artefacts in the final angiogram. However, in the case of small eye movements, the determination of a robust threshold may not be possible because such a threshold would be at the level of a useful signal, and therefore angiograms not influenced by eye movements could be removed. Another problem with method B is that by removing the influenced angiograms, the number of angiograms that are taken into account during the combination into the final angiogram (e.g. step 6) is reduced, and so the quality of the final angiogram may be degraded. This problem can be dealt with by increasing the number of repetitions of the B-scans. However, such an approach increases the acquisition time, and extends the time for the execution of the OCTA process. Thus, this is not an efficient way of dealing with the problems encountered in method B.

Non-patent literature 3 discusses another known technique in structural OCT imaging where a single shift between adjacent B-scans is determined and corrected. However, such method is not efficient enough to entirely remove the artefacts in OCTA imaging as a result of eye movements.

Patent publication number WO2006/077107 discusses a technique that tries to solve the problem of rapid eye movements during long acquisition of data by collecting at least two acquisitions of data sets in an orthogonal direction. Based on a similarity function, it combines both data sets into a single data set free of movements. This method can efficiently reduce the influence of rapid eye movements which creates the distortion of two-dimensional scanning positions. However, compensation of head-induced influence is not discussed in detail. Moreover, the method is not suitable enough to align the B-scan images at the same position of the eye.

Therefore, an approach to reduce the influence of eye movement during OCTA measurement is desired in order to maintain high quality OCTA images. In particular, there is a need for reducing the influence of eye movement caused by head-induced movements of a patient during OCTA measurement. Moreover, an approach to reduce the influence of eye movement not only during OCTA measurement but also during OCT measurement is desired.

Non-Patent Literature

Non-patent literature 1: Jia, Y., Tan, O., Tokayer, J., Potsaid, B., Wang, Y., Liu, J. J., Huang, D., "Split-spectrum amplitude-decorrelation angiography with optical coherence tomography", Optics Express, 20(4), 4710-4725, 2012.

Non-patent literature 2: Enfield, J., Jonathan, E., & Leahy, M., "In vivo imaging of the microcirculation of the volar forearm using correlation mapping optical coherence tomography (cmOCT)", Biomedical Optics Express, 2(5), 1184-1193, 2011.

Non-patent literature 3: T. Bajraszewski, M. Wojtkowski, P. Targowski, M. Szkulmowski, A. Kowalczyk, "Three dimensional in-vivo imaging by spectral OCT", Proc. of SPIE vol. 5316, pp. 226-232, 2004.

SUMMARY OF THE INVENTION

According to a first aspect of the present invention a method is provided for compensating for motion artefacts in Optical Coherence. A B-scan set including a plurality of B-scan OCT images acquired at least a position corresponding to a target position of a fundus of an eye is acquired. The plurality of B-scans within the B-scan set is aligned using a first alignment process and a second alignment process. The second alignment process is performed on the B-scan images within the B-scan set aligned by the first alignment process. The first alignment process aligns the B-scan images within the B-scan set at a first resolution in at least an axial direction, and the second alignment process aligns the B-scan images within the B-scan set aligned in the first alignment process at a second resolution being a higher resolution than the first resolution in at least the axial direction.

In one embodiment, an alignment range of the second alignment process is smaller than an alignment range of the first alignment process. The first alignment process and the second alignment process may also be performed in the horizontal direction of the B-scan images. The second alignment process may be performed to obtain a shift value in the second resolution to align B-scan images within the B-scan set. The shift value may be calculated by using average decorrelation values calculated between B-scan images within the B-scan set. The second alignment process may include determining for B-scans within the B-scan set, a shift amount, and applying the shift amount to a second B-scan within the B-scan set, so that the second B-scan within the B-scan set is shifted such that the second B-scan is matched with a first B-scan within the B-scan set. Each of the B-scan images may be divided into a plurality of portions, and the second alignment process may be performed on each corresponding portion of B-scans within the B-scan set.

The second alignment process may include determining a shift amount between the corresponding portions of B-scans within the B-scan set, and applying the shift amount to the corresponding portion of a second B-scan within the B-scan set, so that the corresponding portion of the second B-scan within the B-scan set is shifted such that the corresponding portion of the second B-scan is matched with the corresponding portion of a first B-scan within the B-scan set.

In one embodiment, the method may further comprise determining retinal layers of the fundus in the B-scan images, wherein the second alignment process is performed based on the determined retinal layers.

The determined retinal layers may include at least one of the boundary of the Vitreous body and the Inner Limiting Membrane, and the boundary of the Retinal Pigmented Epithelium of the fundus. The method may also further comprise calculating an OCT angiogram from the aligned B-scans within the B-scan set, wherein the OCT angiogram is a motion contrast data set related to blood flow information.

In another embodiment, a system for compensating for motion artefacts in Optical Coherence Tomography is provided. The system may comprise an OCT apparatus for obtaining a plurality of B-scan sets including a plurality of B-scan OCT images acquired at least a position corresponding to a target position of a fundus of an eye and a data processing apparatus for performing the method according to claim 1 to generate an angiogram of the fundus.

According to an aspect of the present application, a computer readable storage medium storing a computer program for causing a computer to execute a method for compensating for motion artefacts in Optical Coherence Tomography is provided. The method comprising acquiring a B-scan set including a plurality of B-scan OCT images acquired at least a position corresponding to a target position of a fundus of an eye; and aligning the plurality of B-scans within the B-scan set using a first alignment process and a second alignment process.

The second alignment process may be performed on the B-scan images within the B-scan set aligned by the first alignment process. The first alignment process may align the B-scan images within the B-scan set at a first resolution in at least an axial direction, and the second alignment process may align the B-scan images within the B-scan set aligned in the first alignment process at a second resolution being a higher resolution than the first resolution in at least the axial direction.

According to the aspects of the present invention, the performance of OCTA processing in terms of both the execution time of calculations, and also the quality of the angiograms can be improved with respect to conventional arrangements. In particular, the performance of OCTA processing in terms of removal of motion artefacts caused by movement of a patient's head and/or eye from OCT angiograms, especially OCTA maps, can be improved.

BRIEF DESCRIPTION OF THE DRAWINGS

FIG. 5A shows the so called bulk motion artefacts as a result of eye movements during OCT angiography measurement; FIG. 5B shows how applying rough alignment improves OCTA en-face maps; and FIG. 5C shows how applying precise alignment after rough alignment removes all horizontal lines from the OCTA en-face map.

FIG. 13A is an example of OCTA result influenced by transversal head movements; FIG. 13B shows the shift value $\delta z_{match}$ distribution along line y=107 of FIG. 13A; and FIG. 13C shows the shift value $\delta z_{match}$ distribution along line y=19 of FIG. 13A.

DESCRIPTION OF THE EMBODIMENTS

Embodiments of the present invention will now be described, by way of example only, with reference to the accompanying figures. Each of the embodiments of the present invention described below can be implemented solely or as a combination of a plurality of the embodiments or features thereof where necessary or where the combination of elements or features from individual embodiments in a single embodiment is beneficial.

Definitions

A technique called "Zero padding" is used for increasing the resolution of Fourier Transformation (FT) results by adding additional samples with the value 0 to an input signal prior FT. It is defined by the coefficient κ which is defined as ratio κ=Npd/N, where Npd is a number of samples after applying the zero-padding procedure. If κ=1, then Npd=N and the result of the FT has N/2 independent result points (for real signals analysis). If κ=4, then Npd=4N and the FT result has 2N points. In general, the FT result has an increased resolution by κ factor.

One "principal pixel" is defined as one bin (frequency resolution) of the FFT calculated from interferograms without applying the zero padding procedure (κ=1).

One "subpixel" is defined as one bin of the FFT calculated from interferograms by applying zero padding where κ>1. In general the axial size of one subpixel=1/κ of axial size of a principal pixel. The subpixel resolution can be obtained using methods other than FFT with zero padding, for example by linear interpolation or cubic interpolation.

First Embodiment

A first embodiment will be described with reference to FIGS. 4 to 9.

Figure 1:
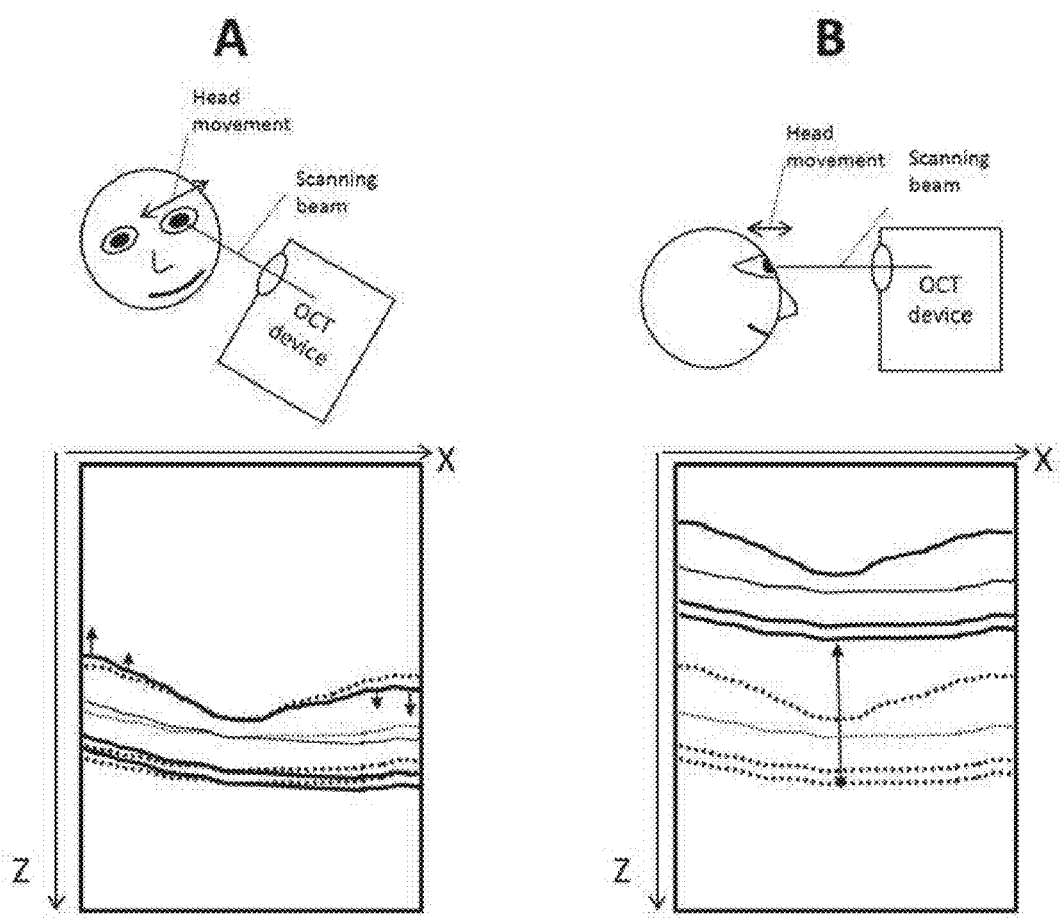
FIG. 1 is a diagram showing an example of the influence of transverse head movements and longitudinal head movements on OCT tomograms.
Figure 2:
FIG. 2 shows a 3×3 mm region of an in vivo OCTA projection map influenced by eye movements.
Figure 3:
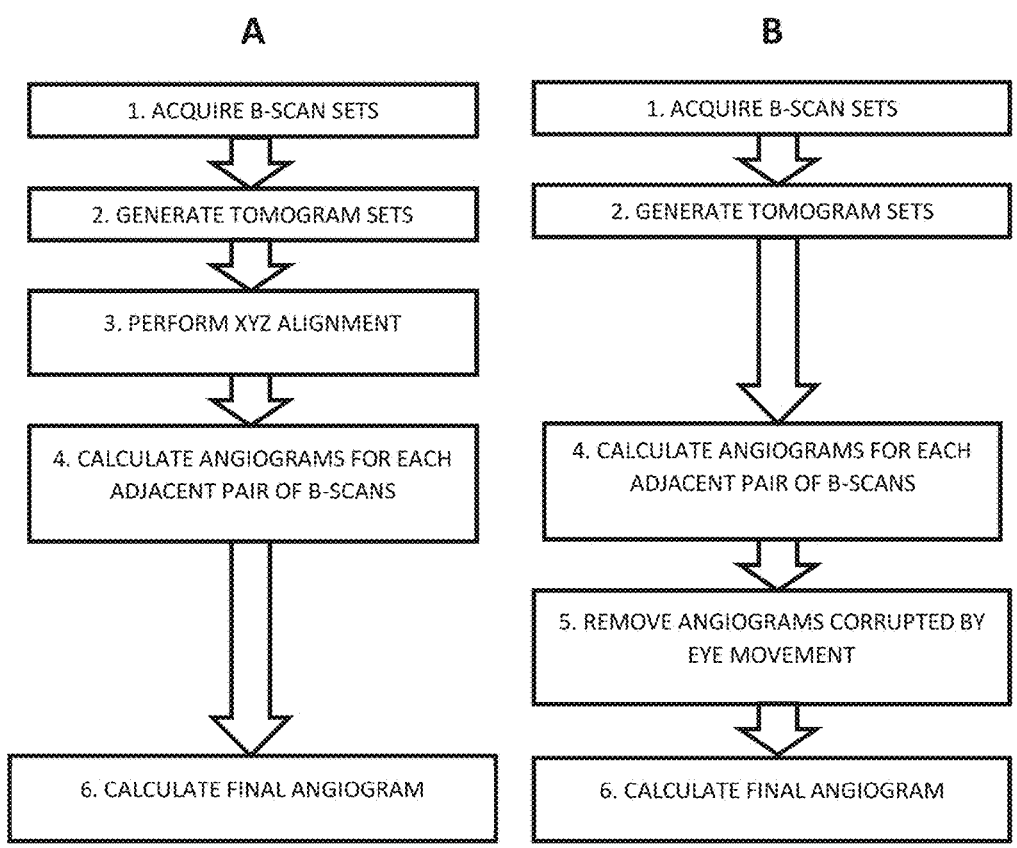
FIG. 3 is a flow diagram showing two conventional arrangements for OCTA processing to reduce the influence of eye movement.
Figure 4:
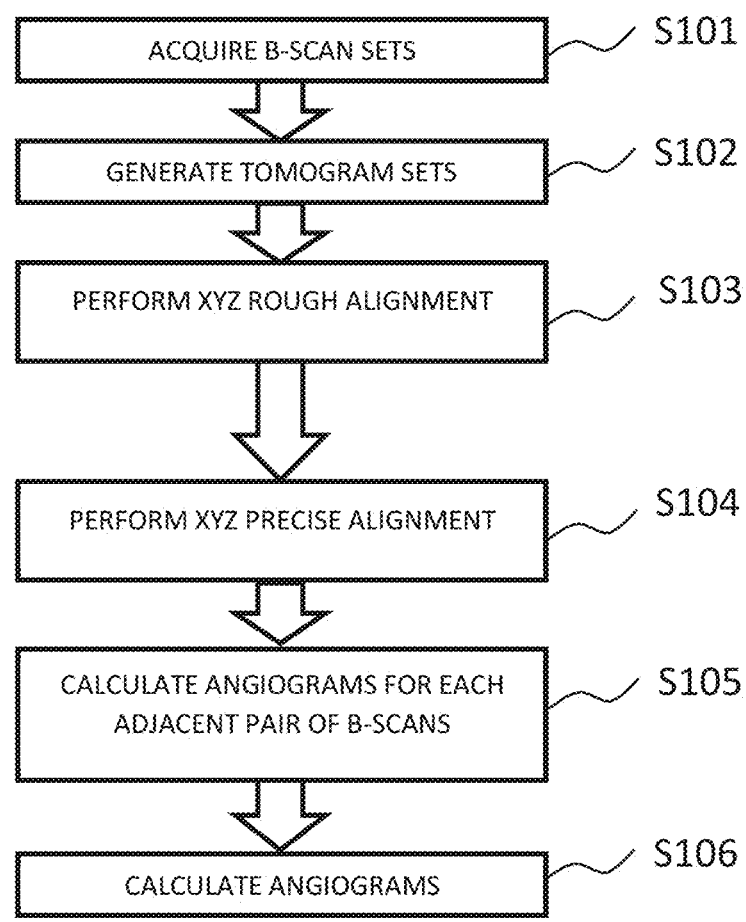
FIG. 4 shows a block flow diagram for calculating OCTA angiograms with eye bulk motions compensation according to an embodiment.

FIG. 4 shows a block flow diagram for calculating OCTA angiograms while compensating for eye motions during OCTA measurement according to this embodiment. This flow is applied to each acquired set of B-scans.

In step S101 a number of B-scan sets are acquired of a fundus. A B-scan set is defined as a number of repeated B-scans (NoR) taken at a particular scanning time of Y or X scan position (in general the position of the slow scan axis). Ideally, the B-scan set includes a plurality of B-scans at a target position of the fundus of the eye. However, each of the plurality of B-scans may not be acquired at the same position (the target position) because of the eye movement and imperfect tracking. Therefore, in practice, the B-scan set includes the plurality of B-scans at least a position corresponding to the target position of the fundus. For example, if NoR=8, eight B-scans are repeated (or acquired) at the particular slow-axis position. From these eight B-scans, at least seven angiograms (NoR−1) can be obtained if each angiogram is calculated from B-scan(i) and B-scan(i+1), where i=1 . . . 8. More angiograms can be obtained if non-neighbour B-scans are used, e.g. B-scan(i) and B-scan (I+2). If an entire examination consists of for example 300 B-scan sets and each B-scan set consists of 8 B-scans, then the total number of B-scans taken during the examination is 300*8=2400 B-scans. Of course, the number of B-scans in a B-scan set is not limited to eight, any number of B-scans may be chosen. For example, at least three B-scans may be chosen as the B-scans set. Increasing the number of B-scans may improve the quality and reliability of detection of blood vessels but increase measurement time, while decreasing the number of B-scans may speed-up the measurement time but decrease the quality and reliability.

In step S102 structural tomograms are generated with zero-padding κ times (κ>1). A decimation process is performed on the generated tomograms to obtain two kinds of tomograms. One kind having subpixel resolution and the second kind having principal pixel resolution. The subpixel resolution has a higher resolution than the principal pixel resolution. The tomograms with principal resolution are used in a rough alignment process described below, while the tomograms with subpixel resolution are used in a precise alignment process described below.

In step S103 alignment with principal resolution is performed. This is called "rough alignment". The purpose of rough alignment is to compensate for effects caused by longitudinal (axial) head movements (and thus eye-movements) along the Z-axis with the accuracy of the principal pixels (first resolution) of the tomogram. The rough alignment process is applied within each B-scan set, and is applied independently for each set. The rough alignment process will be discussed in more detail below with reference to FIG. 6.

In step S104 an alignment with subpixel resolution is performed on the B-scans roughly aligned in step S103. This is called "precise alignment". The purpose of precise alignment is to compensate for effects induced by transverse movements of a head (and thus eye) as well as residual longitudinal (axial) effects with subpixel accuracy (second resolution). The precise alignment process will be discussed in more detail below with reference to FIG. 8.

In step S105 angiograms are calculated for each adjacent B-scan in a B-scan set aligned precisely in step S104 because the embodiment uses the calculation method of the angiogram similar to non-patent literatures 2, 3. Therefore, for example, if the number of B-scans within a B-scan set is eight, at least seven angiograms per B-scan set are obtained. Of course, other methods for calculating the angiograms can be easily applied.

In step S106 a final angiogram is calculated as a combination of the angiograms obtained in step S105. For example, the combined angiogram may be obtained by averaging, median, or so on.

Figure 5A:
FIGS. 5A to 5C show a comparison of a 3×3 mm region of in vivo OCTA en-face map results.
Figure 5B:
Figure 5C:

FIGS. 5A to 5C show a comparison of a 3×3 mm region of in vivo OCTA en-face map results where no compensation for eye movement is made, and where compensation according to this embodiment is made.

In FIG. 5A no compensation is performed and the eye movements during OCTA measurement has resulted in so called bulk motion artefacts (e.g. horizontal lines). In FIG. 5B the application of the rough alignment improves the OCTA en-face map but some horizontal lines are still visible. In FIG. 5C the application of precise alignment after the application of rough alignment removes all horizontal lines from OCTA en-face map.

Figure 6:
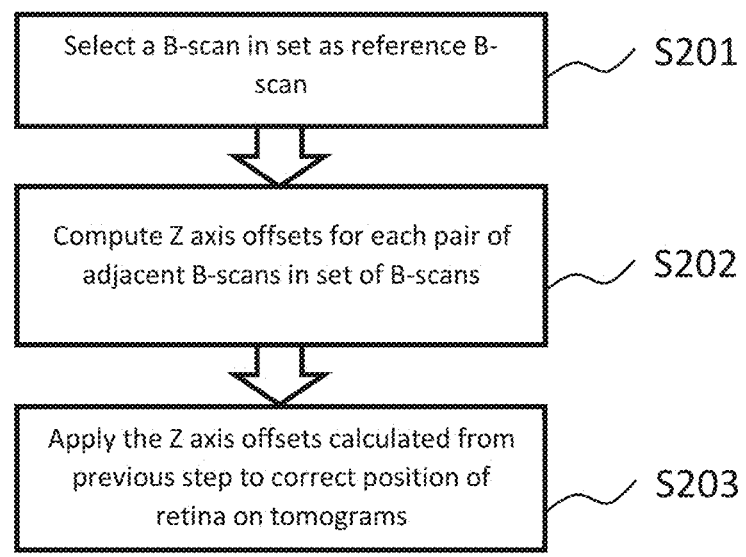
FIG. 6 shows a block flow diagram of the rough alignment process according to an embodiment.

The details of the rough alignment will now be discussed with reference to the block flow diagram shown in FIG. 6. To roughly align all B-scans in the Z-axis within each B-scan set, global Z-axis offsets are determined between a B-scan reference and each other B-scan in the B-scan set using standard techniques, e.g. by correlation of two images. Accordingly, in step S201 a B-scan is selected from the B-scan set and is used as a reference. The reference B-scan can be selected using any suitable criteria. For example the reference B-scan could be the first B-scan, or the B-scan with the highest intensity and/or best sharpness.

In step S202 using the selected B-scan reference the Z-axis offset for each pair of adjacent B-scans in a B-scan set is determined. Then in step S203 the global Z-axis offsets are applied to each B-scan within a B-scan set except the reference B-scan to correct the position of the retina on each of them. This procedure is applied to all B-scan sets independently.

Figure 7:
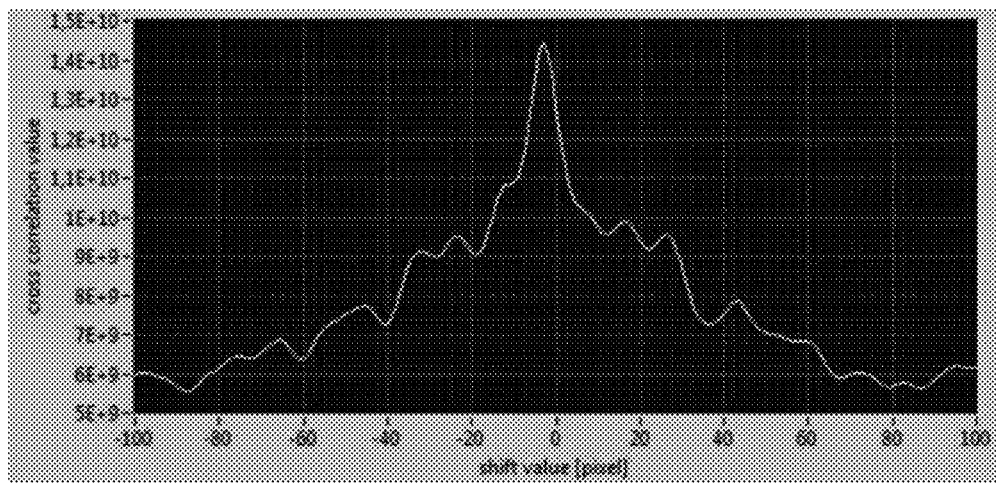
FIG. 7 shows an example of cross correlation as a function of shift amount.

An example of cross-correlation of two B-scan images as a function of shift value in the Z-direction is shown in FIG. 7. In FIG. 7, the X-axis represents shift value in the Z-direction of the B-scan image and the Y-axis represents the cross correlation value. A desirable value of the X-axis shift value would be having the maximum peak of the cross-correlation value at a shift value of zero (0). However, as shown in the example in FIG. 7 the maximum cross correlation value is located at a shift value of −3 principal pixels in the Z-direction of the B-scan image. This means that a correlated image is shifted by −3 principal pixels in relation to the reference B-scan.

Figure 8:
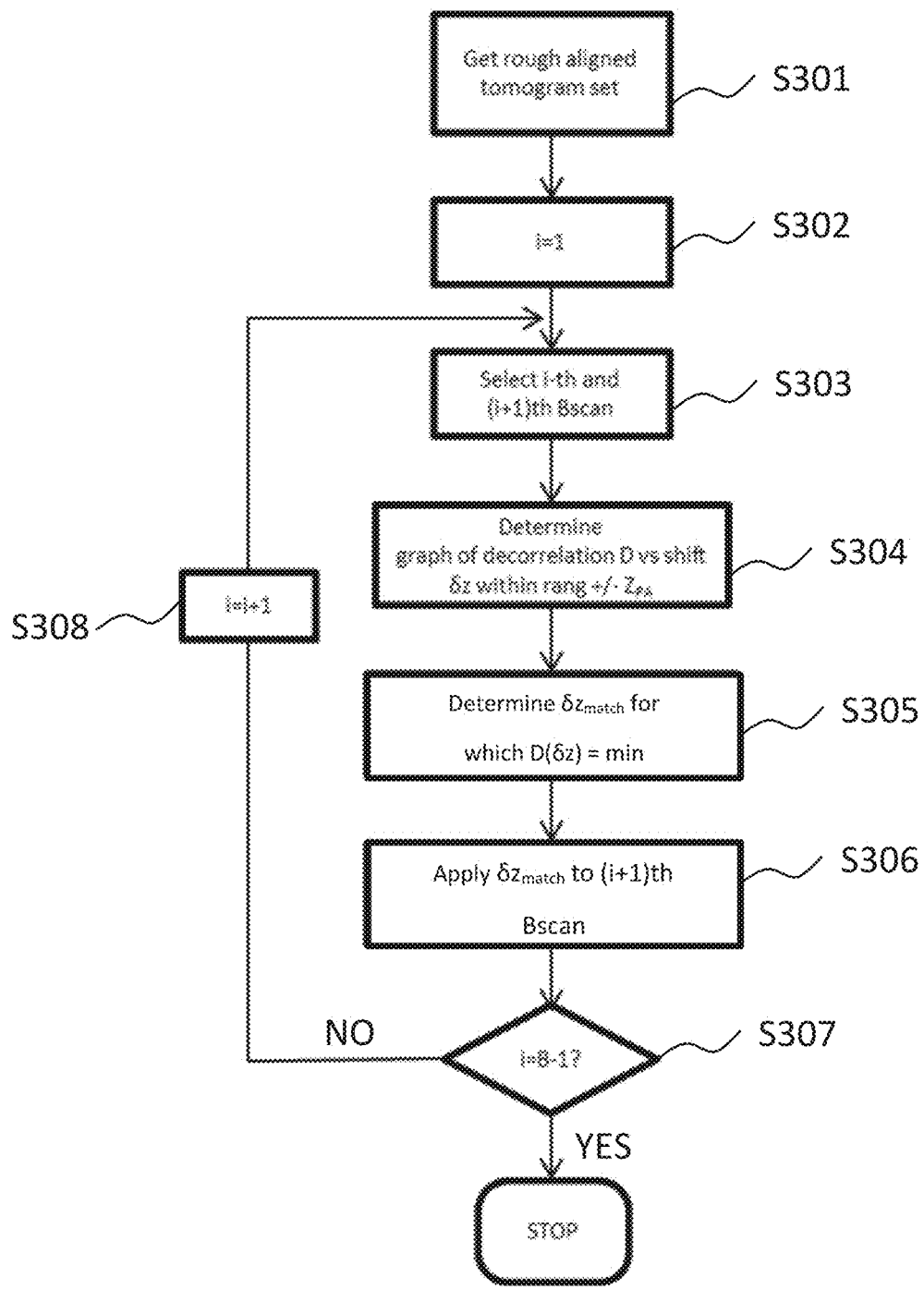
FIG. 8 is a flow diagram of the precise alignment procedure according to the first embodiment for a single B-scan set.

Next the details of the precise alignment will be discussed with reference to the flow diagram shown in FIG. 8. The precise alignment in the Z-axis is performed on the roughly aligned tomograms.

In step S301 the tomogram set roughly aligned in the rough alignment is used as the basis for the precise alignment. In step S302 the value of parameter i is set to 1. The value i represents the number of B-scan pairs within a B-scan set. For example, if the B-scan set contains eight B-scans there are seven B-scan pairs; the first pairing being the first and second B-scans, the second pairing being the second and third B-scans, and so on. Accordingly, the value of i=1 represents the first pair of B-scans (e.g. the first and second B-scans) within the B-scan set, while i=2 represents the second pair of B-scans (e.g. the second and third B-scans) within the B-scan set, and so on. Setting i=1 in step S302 selects the first B-scan pair.

In step S303 the $i^{th}$ B-scan and $(i+1)^{th}$ B-scan within a B-scan set are selected. In other words, when i=1 the first B-scan (i=1) and the second B-scan (1+1=2) within the B-scan set are selected.

In step S304 a relationship between an average decorrelation value $D_i(\delta z)$ versus shift value $\delta z$ is calculated for the $i^{th}$ B-scan pair selected in step S303. The average decorrelation value $D_i$ is an average value of the decorrelation value $d_i$ for two B-scans in a single B-scan set taken at the same slow axis position (X or Y scan position). To calculate the decorrelation value $d_i(x, z, \delta z)$ for the $i^{th}$ B-scan pair (the $i^{th}$ B-scan and the $(i+1)^{th}$ B-scan selected in step S303), the same equations that are used for motion contrast calculation in OCTA image reconstruction can be used:

$$d_i(x, z, \delta z) = 1 - \frac{2 \cdot I_i(x, z) \cdot I_{i+1}(x, z + \delta z)}{I_{i,k}^2(x, x) + I_{i+1,k}^2(x, z + \delta z)}, \quad (1)$$

where I(x, z) is an intensity of a signal at location (x, z) in the tomogram in subpixels, $\delta z$ is the shift value in subpixels, and k is the number of the A-scan.

The average decorrelation value $D_i$ can be calculated as:

$$D_i(\delta z) = \frac{1}{Nz * Nx} \sum_{z=1}^{Nz} \sum_{x=1}^{Nx} di(x, z, \delta z), \quad (2)$$

where Nz, Nx is the number of the pixels in a B-scan in subpixels in the Z-axis direction and the X-axis direction.

Figure 9:
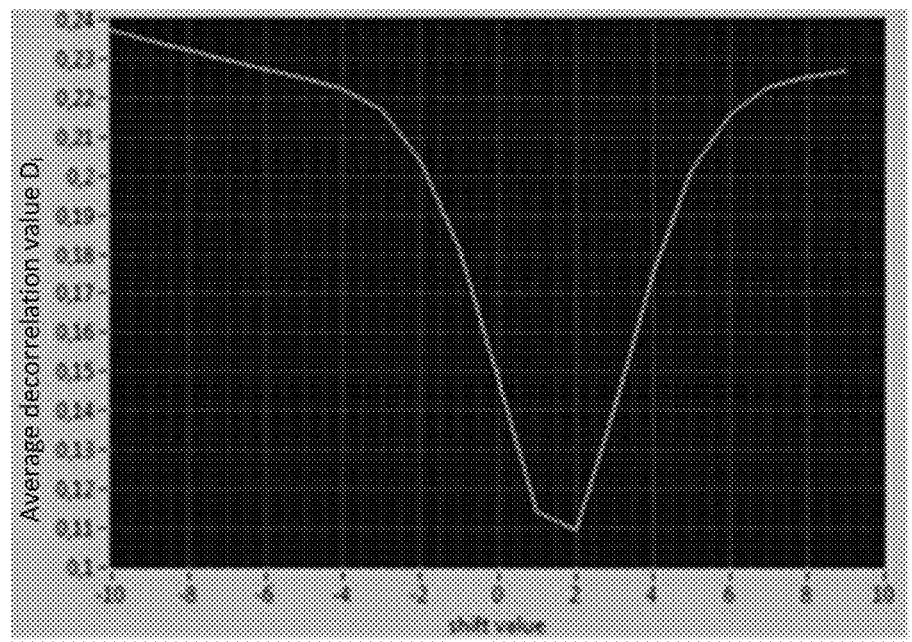
FIG. 9 shows an example of the averaged decorrelation signal calculated as a function of the shift value.

For each of the two B-scans in a single B-scan set (the $i^{th}$ B-scan pair), a graph of the average decorrelation value $D_i(\delta z)$ versus a shift value $\delta z$ is generated within a range $+/-Z_{P4}$. An example of such a graph is shown in FIG. 9. The value $Z_{P4}$ represents an alignment range, and it is typically smaller than the alignment range of the rough alignment.

In FIG. 9 the shift value $\delta z$ is represented on the X-axis, while the average decorrelation value $D_i(\delta z)$ is represented on the Y-axis. In this example, the shift value range is equal $+/-10$ subpixels to clearly demonstrate how the average decorrelation value depends on the shift value. The analysed tomogram is shifted in relation to its original position subpixel by subpixel.

In step S305 the shift value $\delta z_{match}$ corresponding to the minimum value of the average decorrelation $D_i(\delta z)$ is determined. The minimum average decorrelation position is at the best or suitable shift amount that provides the best match (i.e. least differences) between the two B-scans in a single B-scan set (the $i^{th}$ B-scan pair). In FIG. 9 the minimum average decorrelation value is obtained at the shift value $\delta z_{match} = -2$.

In step S306 the determined shift value $\delta z_{match}$ is applied to the $(i+1)^{th}$ B-scan. In other words, in this example the $(i+1)^{th}$ B-scan is shifted by 2 subpixels.

In step S307 it is determined if the value of i equals the number of B-scan pairs within the B-scan set (the number of B-scans minus one B-scan, i.e. i=B−1, where B is the number of B-scans within the B-scan set). Thus, if there are 8 B-scans within a B-scan set, step S307 checks whether i is equal to 7. If i does not equal B−1, then the flow proceeds to step S308 where the value of i is incremented by one and the process of steps S303 to S307 are repeated. In this manner steps S303 to S307 are repeated for each $i^{th}$ B-scan pair within each B-scan set, until all B-scan pairs have been processed.

The accuracy of the determination of the displacement can be increased by increasing the value of zero padding, or by applying a fitting method to the obtained results (for example fitting polynomial using a least squares method).

According to the process of this embodiment a method for compensating for motion artefacts in Optical Coherence Tomography Angiography is provided. A plurality of B-scan sets are acquired, where each B-scan set includes a plurality of B-scan OCT images acquired at a position of a fundus of an eye. The B-scans within each B-scan set are aligned using a first alignment process and a second alignment process. The second alignment process is performed on the B-scan images within each B-scan set aligned by the first alignment process. An OCT angiogram from the aligned B-scans within each B-scan set is generated.

The first alignment process aligns the B-scan images within each B-scan set at a first resolution (principal pixel) in at least an axial (Z-axis) direction, and the second alignment process aligns each adjacent B-scan pair in each B-scan set aligned by the first alignment process at a second resolution (subpixel) in at least the axial (Z-axis) direction. The second resolution (subpixel) is a higher resolution than the first resolution (principal pixel).

In the second alignment process (precise alignment), for each pair of B-scans within a B-scan set, a shift amount is calculated and applied to the second $((i+1)^{th})$ B-scan of the pair, so that the second $((i+1)^{th})$ B-scan of a pair is shifted such that it has the best match, or correlation, with the first $(i^{th})$ B-scan of the B-scan pair.

The disclosed method introduces to OCTA processing an algorithm for eye movement compensation by performing rough and precise alignment. The precise alignment is performed with subpixel accuracy. The precise alignment is performed using the averaged value of the decorrelation coefficient value (minimum of the averaged value of decorrelation coefficient as a function of shift value). Thus the process is able to determine the shift value between adjacent B-scans within a B-scan set.

According to this embodiment, the performance of OCTA processing in terms of both the removal of motion artefacts from OCT angiograms, especially OCTA maps, and the execution time of calculations, can be improved with respect to conventional arrangements. Furthermore, the quality of the angiograms can be improved.

Second Embodiment

The second embodiment is different from the first embodiment in that a different precise alignment process is used. Otherwise, the second embodiment follows the same procedures as the first embodiment shown in FIG. 4. By using the precise alignment process of this embodiment, the accuracy of the precise alignment is increased over that used in the first embodiment.

Figure 10:
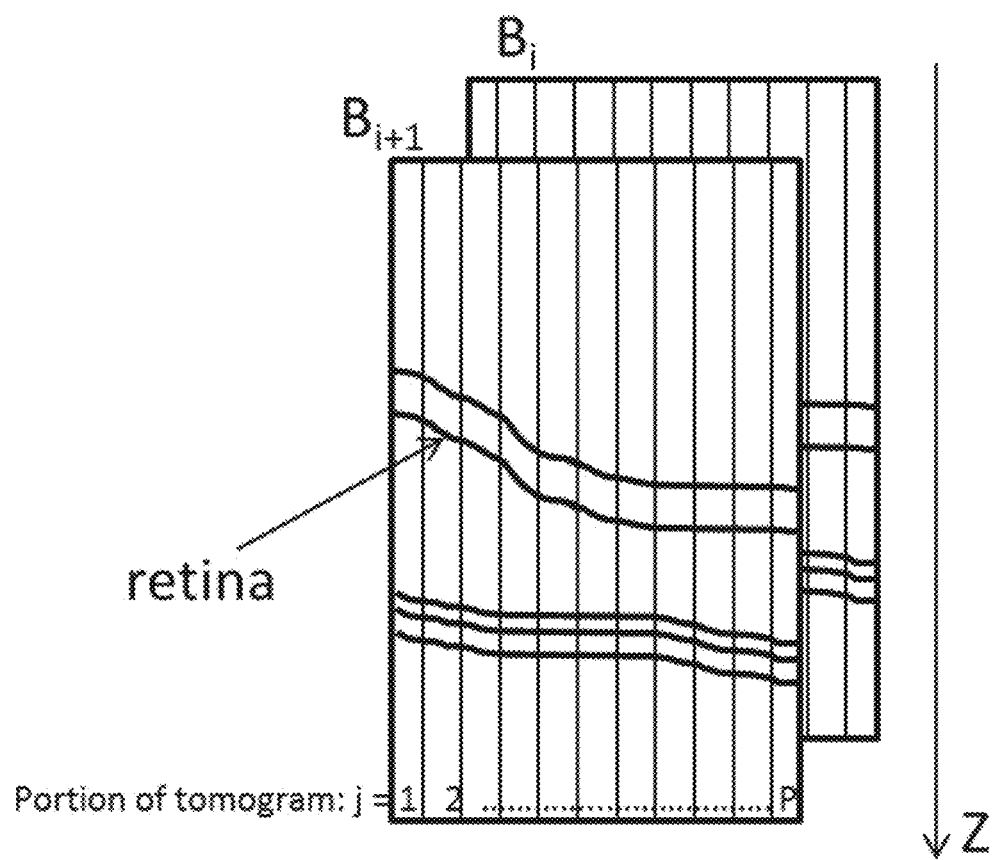
FIG. 10 shows an example of how B-scans are divided into smaller portions according to a second embodiment.

The second embodiment differs from the first embodiment in that each B-scan pair is divided into smaller portions. For each pair of adjacent B-scans indexed by i, the B-scan pair is divided onto P smaller portions (or blocks) indexed by j. This is illustrated in FIG. 10, where P denotes the number of portions a B-scan is divided into, and B is the number of the B-scans within a B-scan set (e.g. 1, 2, 3, . . . , B). In the example shown, the B-scans are divided into 11 portions.

However, the embodiment is not limited to this number of divisions. The B-scans may be divided in any suitable number of divisions.

Figure 11:
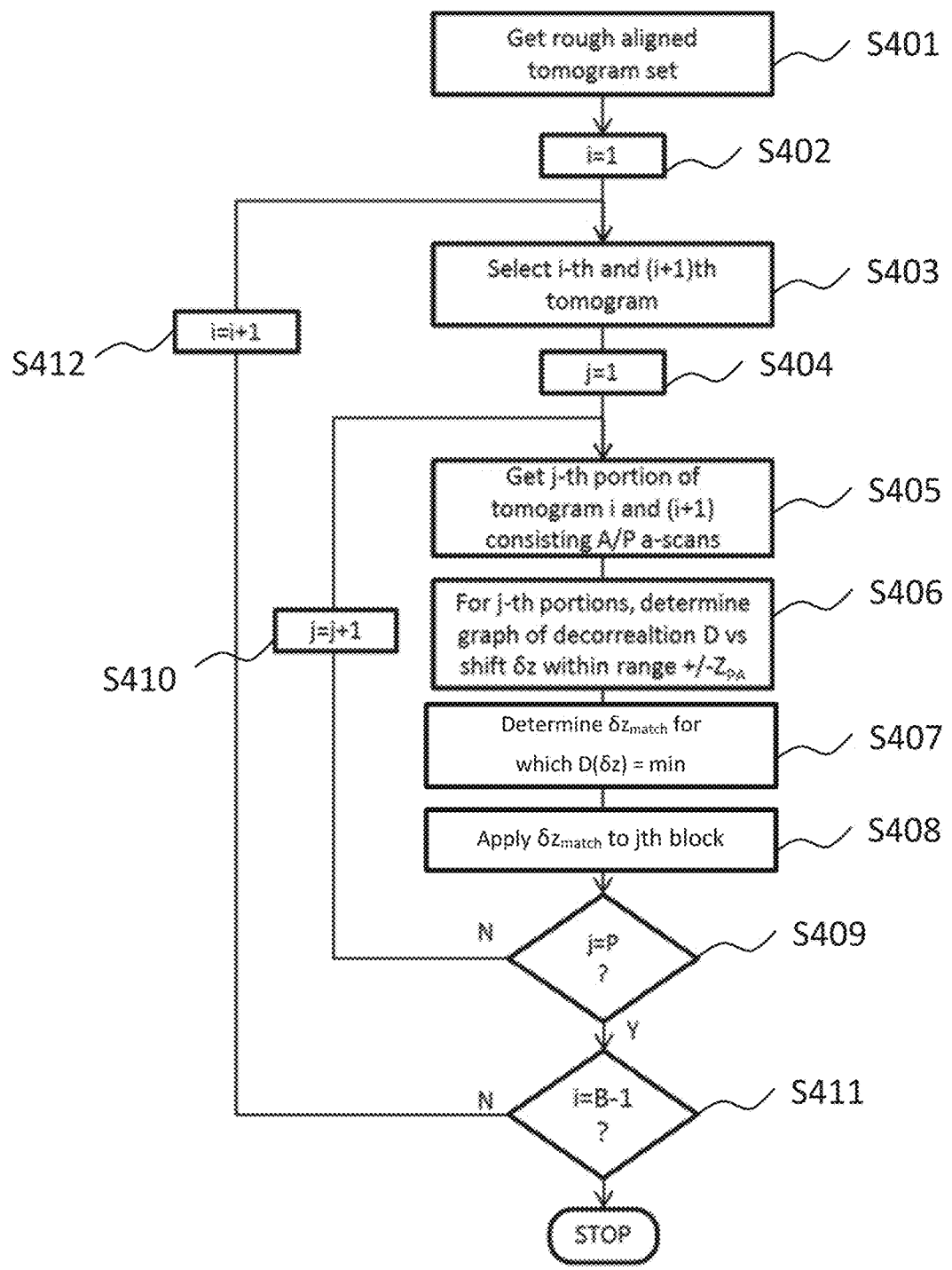
FIG. 11 shows a flow diagram of the precise alignment procedure according to the second embodiment for a single B-scan set.

FIG. 11 shows a flow diagram of the precise alignment in this embodiment for a single B-scan set. It is repeated for all B-scan sets of an entire examination.

Similar to the first embodiment, in step S401 the precise alignment in the Z-axis is performed on the roughly aligned tomograms (roughly aligned in step S103). In step S402 the value of i (the $i^{th}$ B-scan pair) is set to 1. In step S403, similarly to step S303, the $i^{th}$ B-scan and $(i+1)^{th}$ B-scan within a B-scan set is selected. In other words, when i=1 the first and second B-scans within the B-scan set are selected.

In step S404 the value of j is set to 1, thus setting the value of j to the first portion P of the B-scan pairs. In step S405 the $j^{th}$ portion of the tomograms of the $i^{th}$ B-scan and the $(i+1)^{th}$ B-scan are selected. In other words, when i=1 and j=1 the first portion (p=1) of the tomograms of the first and second B-scans is selected.

In step S406 for the selected portion j of the tomograms, the average decorrelation D versus shift δz within a range $+/-Z_{P4}$ is calculated. The average decorrelation value D is an average value of decorrelation for each partial angiogram resulting from a calculation of the decorrelation d of the $j^{th}$ portions of the B-scan pair. To calculate the decorrelation value $d_{i,j}(z)$ for the $i^{th}$ B-scan pair and $x^{th}$ A-scan at a certain depth z, the same equations that are used for motion contrast calculation in OCTA image reconstruction can be used:

$$d_{i,j}(x, z, \delta z) = 1 - \frac{2 \cdot I_{i,k}(x, z) \cdot I_{i+1,k}(x, z + \delta z)}{I_{i,k}^2(x, x) + I_{i+1,k}^2(x, z + \delta z)}, \quad (3)$$

where I(z) is an intensity of a signal at depth Z.

The average decorrelation value $D_{i,j}$ can be calculated using:

$$D_{i,j}(\delta z) = \frac{1}{Nz * Np} \sum_{z=1}^{Nz} \sum_{x=1}^{Np} d_{i,j}(x, z, \delta z), \quad (4)$$

where Nz is the number of the pixels in a B-scan in a Z direction in subpixels, and Np is the number of the pixels of a divided small portion of a B-scan in the X direction in subpixels.

Figure 12:
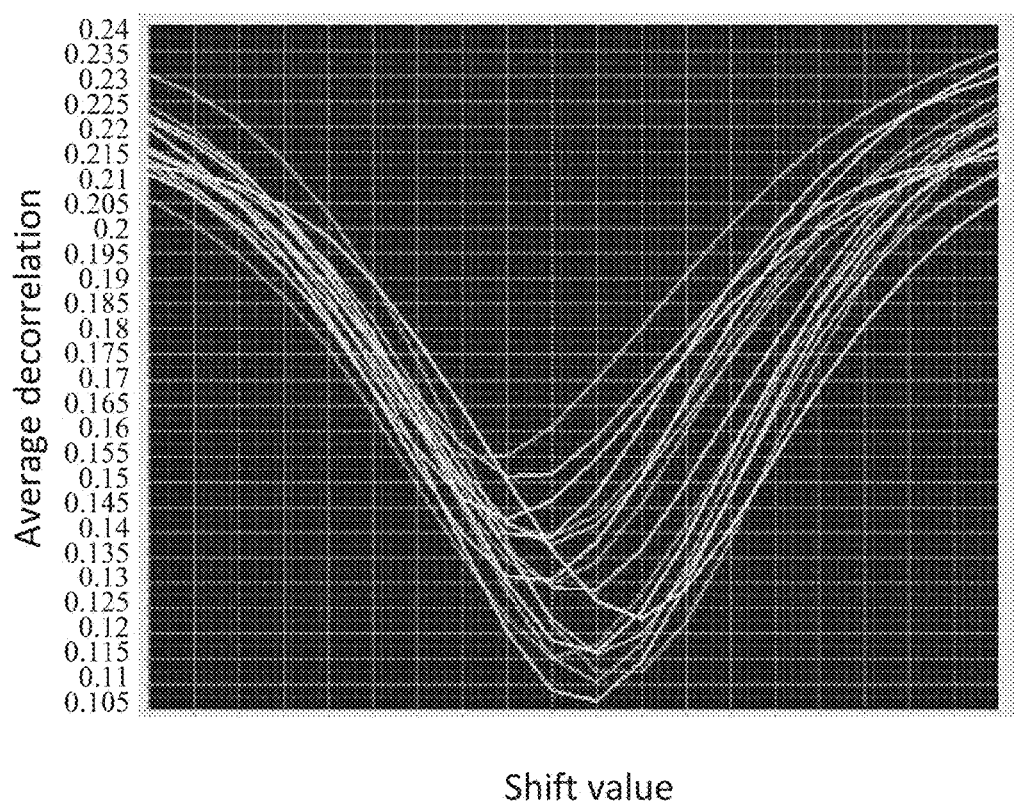
FIG. 12 is a graph representing the average decorrelation value D versus shift value δz for several portions of a B-scan pair.

As will be discussed below in relation to step S409, the value of j is incremented for all portions P of the tomograms. Accordingly, the average decorrelation is calculated for all of the portions of the tomograms of all B-scan pairs. FIG. 12 shows an example of the average decorrelation D(δz) for several portions P of a B-scan pair.

To ensure a high dynamic range of the functions presented in FIG. 12, it is advantageous to calculate the average decorrelation from a selected portion at a depth (z-axis) limited by the area of a signals existence. To find such limits, a layer detection algorithm cab be performed to determine boundaries between layers of the retina (described in the third embodiment below in detail). Then, the average decorrelation may be calculated between a vitreo-retinal interface and RPE/Choroid interface. Any other boundaries may also be used. In particular, the depth range for the average decorrelation may be set arbitrarily, or the entire depth size can be used. In the latter case, however, the average decorrelation graph shown FIG. 12 may have smaller dynamics (e.g. the minimum may be not so deep). This may decrease the reliability of accurately detecting the shift value at the minimum average decorrelation.

Equation (3) gives the decorrelation value $d_{i,j}$ as a function of shift δz, which varies within a $+/-Z_{P4}$ range. This range can be defined by theoretical considerations of the transverse head movements assuming a certain amplitude of head movement in a worst case (e.g. a patient having a head-fixation problem e.g. due to Parkinson disease). The amplitude of head movements will transfer to movement of a scanning beam pivot against the eye's pupil, and the optical path variation for peripheral scanning beams will be deduced. Alternatively, the range can be determined empirically by providing intentional transverse movement of the head during acquisition of the data or by statistical analysis of a representative sample of clinical data.

In step S407 the shift value $\delta z_{match}$ (j) corresponding to the minimum value of the average decorrelation $D_i(\delta z)$ is determined for the current portion j. In other words, the shift value at the position of the minimum value of the average decorrelation (Dmin) is determined as the shift value $\delta z_{match}$ (j), i.e. $D(\delta z_{match})=D_{min}$. This represents the best match (i.e. least differences) between the two portions of the B-scan pair. An example of the variations of the shift value over different portions of the B-scans is described in more detail below with reference to FIG. 13.

In step S408 the determined shift value $\delta z_{match}$ (j) is applied to the $j^{th}$ portion (block) of the $(i+1)^{th}$ B-scan. In other words, if i=1 and j=1 the determined shift value $\delta z_{match}$ (j) is applied to the first portion P of the second B-scan.

In step S409 it is determined if the value of j equals the total number of portions P. If j does not equal the total number of portions the flow proceeds to step S410 where the value of j is incremented by 1 so that the processing in steps S405 to S408 is carried out on the next portion of the $i^{th}$ and $(i+1)^{th}$ B-scans. In this manner, steps S405 to S408 are performed for all portions P of the $i^{th}$ and $(i+1)^{th}$ B-scans until the value of j=P, and so all portions have been processed. Once j=P the flow proceeds to step S411.

In step S411 it is determined if the value of i equals the number of B-scan pairs within the B-scan set (the number of B-scans minus one B-scan, i.e. i=B−1, where B is the number of B-scans within the B-scan set). Thus, if there are eight B-scans within a B-scan set, step S411 checks whether i is equal to seven. If i does not equal B−1, then the flow proceeds to step S412 where the value of i is incremented by one and the process of steps S403 to S410 are repeated. In this manner steps S403 to S410 are repeated for each $i^{th}$ B-scan pair within each B-scan set, until all B-scan pairs have been processed. In other words, each portion of each B-scan pair is processed.

According to the above process, for each pair of B-scans within a B-scan set, and for each corresponding portion j of the B-scan pairs, a shift amount between the corresponding portions is calculated and applied to the corresponding portion of the second $((i+1)^{th})$ B-scan of the pair, so that the corresponding portion of the second $((i+1)^{th})$ B-scan of a pair is shifted such that it has the best match, or correlation, with the corresponding portion of the first $(i^{th})$ B scan of the B-scan pair.

Figure 13A:
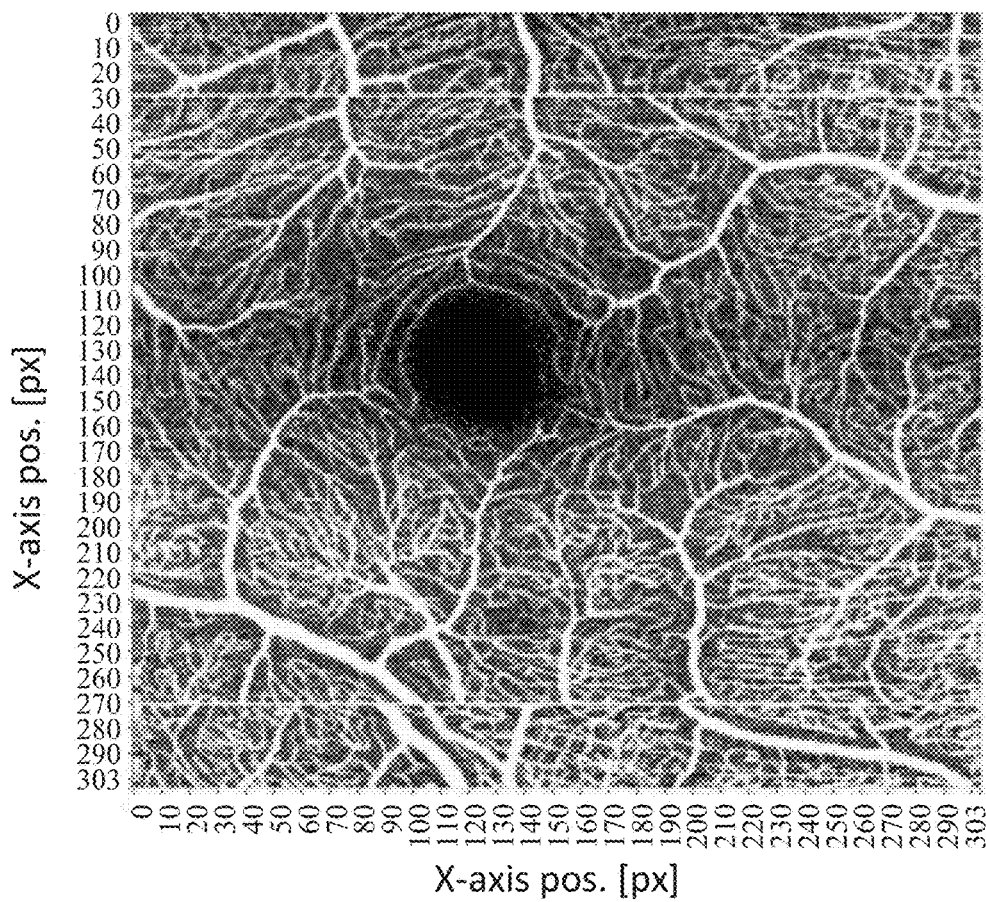
FIGS. 13A to 13C show an example of the results of an OCTA and shift distribution.

FIG. 13A show an example of an OCTA result influenced by transversal head (and thus eye) movements. The OCTA image in FIG. 13A was obtained by averaging seven angiograms obtained from eight repeated B-scans collected within a B-scan set for each y-coordinate. The size of the scanned area is 3×3 mm. During the data acquisition, a volunteer patient provided intentional horizontal movement of the head while keeping the eye fixed on a fixation target of the OCT apparatus. The image was then processed with rough alignment for longitudinal movements and precise alignment applied for compensation of residual longitudinal movements, but without compensation for Z-shifts along the B-scan width.

As shown in FIG. 13A, except for two strong horizontal lines at y=32 and y=270 caused by saccadic eye movements, other weaker horizontal artefacts are caused by the transversal head movement. A characteristic of transversal head movements is that the horizontal artefacts are more visible at peripheral portions, while the centre portion is not so influenced.

Figure 13B:
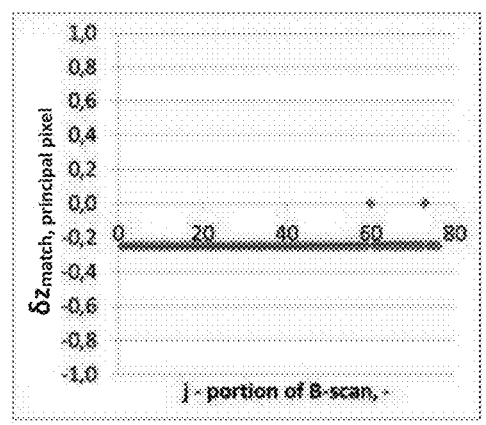
Figure 13C:
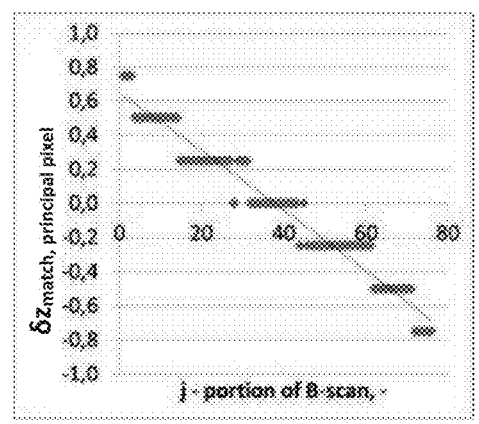

FIG. 13B shows the shift value $\delta z_{match}$ distribution along line y=107 of FIG. 13A and FIG. 13C shows the shift value $\delta z_{match}$ distribution along line y=19 of FIG. 13A. Each B-scan within a B-scan set included 304 A-scans. For the precise alignment, each portion P of a B-scan included 4 A-scans, thus each B-scan was divided into P=304/4=76 portions.

If a distribution of the shift value $\delta z_{match}$ (j) is a constant horizontal line as shown in FIG. 13B, then a single shift value δz would give the best match between two B-scans along the entire width. However, the shift value $\delta z_{match}$ (j) in general may not be a constant value, and the amplitude of a mismatch may be much higher than the longitudinal speckle size. FIG. 13C shows such a case. In this case, precise alignment along the B-scan width is required. From this graph, it can also be deduced that an artefact becomes visible with a mismatch as small as 0.3× the principal pixel size. From this analysis it can be concluded that the minimum κ value would be κ=1/0.3=3.33, or rounding to the highest integer κ=4. For such κ, artefacts caused by transversal head movement can be efficiently eliminated using the processing of this embodiment.

Figure 14:
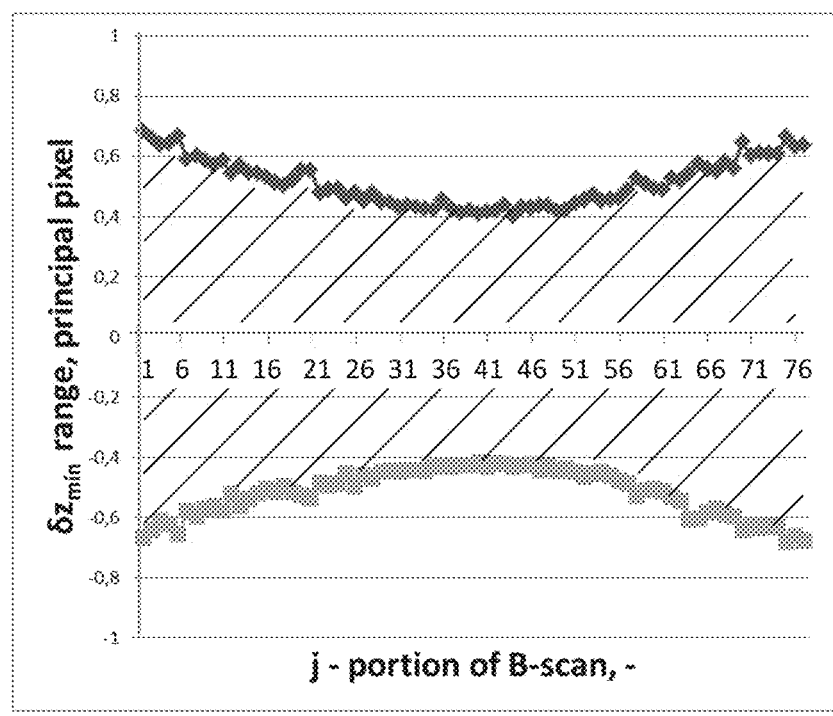
FIG. 14 shows as example of the maximal change of the shift value $\delta z_{match}$ for an entire 3D examination.

Analysing the entire data set, the value of the alignment range $Z_{PA}$ can be found. FIG. 14 shows an area of fluctuation of shift value $\delta z_{match}$ along all B-scan sets for the image shown if FIG. 13A. Thus, FIG. 14 shows the maximum change of the shift value $\delta z_{match}$ for the entire 3D examination. From this analysis it can be concluded that $Z_{PA}$ can be limited to +/−1 principal pixel for a typical 3×3 mm OCTA examination using an OCT apparatus with a 3 μm axial resolution and having 2048 samples of interference signal. However, this range depends on the OCT apparatus performance (especially optical axial resolution and the number of samples of interference signal) as well as the B-scan size and the centre from the optical axis. In practice, in order to maintain a low computation time, $Z_{PA}$ can be determined using a look-up table versus A-scan coordinate from the optical axis.

Although FIGS. 13A to 13C represent a single case study, the applied intentional transversal movements were relatively large, but smaller than the radius of the pupil during examination (about 2 mm). Accordingly, the appropriate value of $Z_{PA}$ may depend of the amount of movement. Alternatively, a margin may be assumed, and $Z_{PA}$ can be increased by some factor, e.g. by factor of 2.

In this embodiment, an algorithm for eye movement compensation by performing rough and precise alignment is provided. The precise alignment is performed with subpixel accuracy (second resolution) for a number of portions of a B-scan. The precise alignment is performed using the averaged value of the decorrelation coefficient value (minimum of the averaged value of decorrelation coefficient as a function of shift value). Thus the process is able to determine the shift value between corresponding portions of adjacent B-scans within a B-scan set.

According to this embodiment, the performance of OCTA processing in terms of both the removal of motion artefacts from OCT angiograms, especially OCTA maps, and the execution time of calculations, can be improved with respect to conventional arrangements. Furthermore, the quality of the angiograms can be improved.

Third Embodiment

The third embodiment differs from the first and second embodiments by including an additional process step between the rough alignment and the precise alignment. In particular, the third embodiment includes the additional step of detecting layers of the retina of a fundus.

Figure 15:
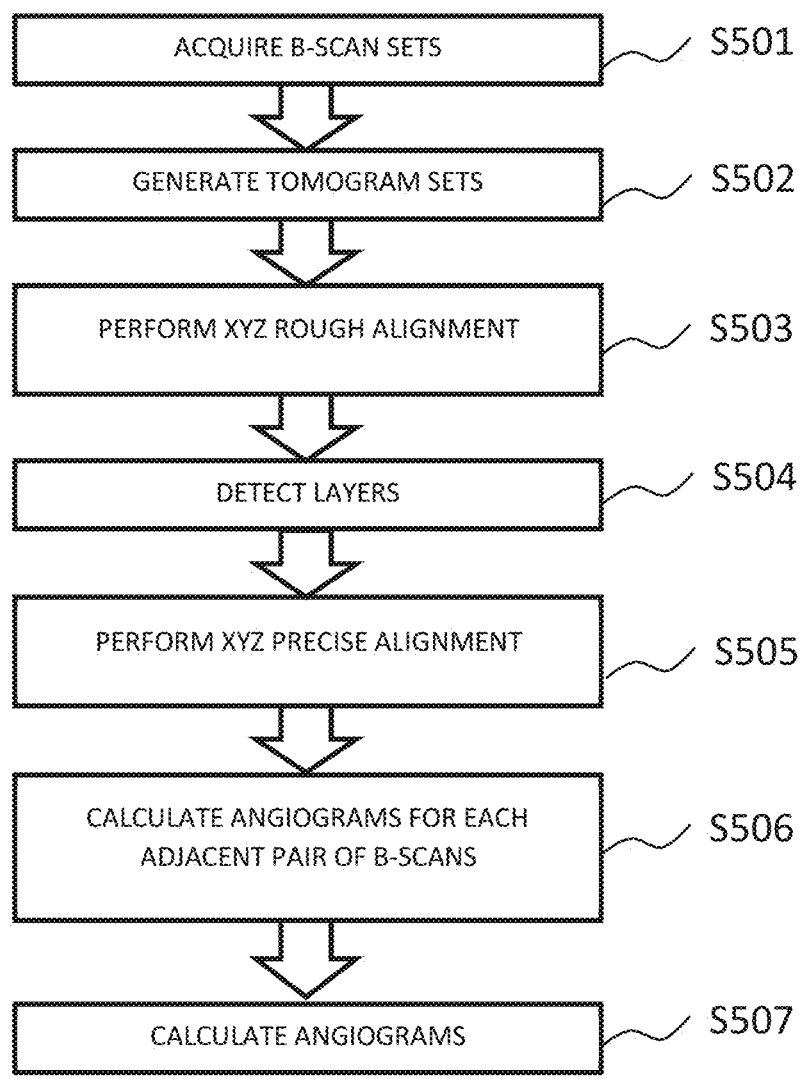
FIG. 15 is a block flow diagram for calculating OCTA angiograms with eye bulk motions compensation according to a third embodiment.

FIG. 15 shows the general block flow diagram for calculating OCTA angiograms with bulk eye motion compensation according to this embodiment. This flow is applied to each of the acquired set of B-scans.

In FIG. 15, steps S501 to S503 are similar to steps S101 to S103 of FIG. 4, and steps S505 to S507 are similar to steps S104 to S106 of FIG. 4.

FIG. 15 includes an additional step, step S504, between the rough alignment S503 and the precise alignment S505.

Steps S501 and S502 are substantially the same as described for steps S101 and S102 of FIG. 4, and so a description of these steps will not be repeated here.

In step S503 a subpixel accuracy alignment to compensate bulk motions of the eye is performed (rough alignment). The rough alignment process is applied within a single set of B-scans and is applied independently for each B-scan set. The rough alignment in step S503 is substantially the same as the rough alignment in step S103 of FIG. 4 and as described with reference to FIG. 6.

When the B-scans are roughly aligned in step S503, in step S504 all of the structural tomograms within the B-scan set are integrated to form an integrated B-scan, and the integrated B-scans are used for layers detection for the entire 3D data set.

In step S505 the precise alignment of the B-scans is performed. This will be described in more detail below. In the step S506 angiograms are calculated for each precisely aligned adjacent B-scans, and in step S507 the final angiogram is calculated as an average of the angiograms obtained in step S506. Steps S506 and S507 are substantially the same as steps S105 and S106 of FIG. 4, and so again the discussion of these steps will not be repeated.

This embodiment differs from the first and second embodiments in that the precise alignment in step S505 is calculated by averaging the decorrelation value $D_{i,j}$ within the scope of specific retinal layers. In particular, instead of using equation (2), equation (5) is used:

$$D_{i,j}(\delta z) = \frac{1}{Nx} \sum_{x=1}^{Nx} \frac{1}{(z1-z0)} \sum_{z=z0}^{z1} d_{i,j}(x, z, \delta z), \quad (5)$$

where $d_{i,j}(x,z,\delta z)$ is the decorrelation value calculated by equation (1), z0 is the bottom boundary of the specific retinal layers, and z1 is the top boundary of the specific retinal layers. (the boundary of the specific retinal layers ("z0" and "z1") are variables at each fast axis (X location.)

In this embodiment, the top of the specific retinal layers is chosen as the boundary of "Vitreous Body" and "Inner Limiting Membrane (ILM)", and the bottom layer is chosen as the boundary of "Retinal Pigmented Epithelium (RPE)".

However, the selection of the top layer and bottom layer is not limited to these layers within the eye, any suitable boundaries may be used.

Thus, in the present embodiment the average decorrelation is limited in the Z-axis by the area of a signals existence between a top layer and a bottom layer. By doing this, the total calculation time for generating the OCTA can be decreased efficiently with respect to the calculation time of the first and second embodiments.

Fourth Embodiment

The first to third embodiments discuss processes for calculating OCTA angiograms while compensating for eye motions during OCTA measurement. In the fourth embodiment a system (or apparatus) is provided for calculating the OCTA angiograms while compensating for eye motions during OCTA measurement.

Figure 16:
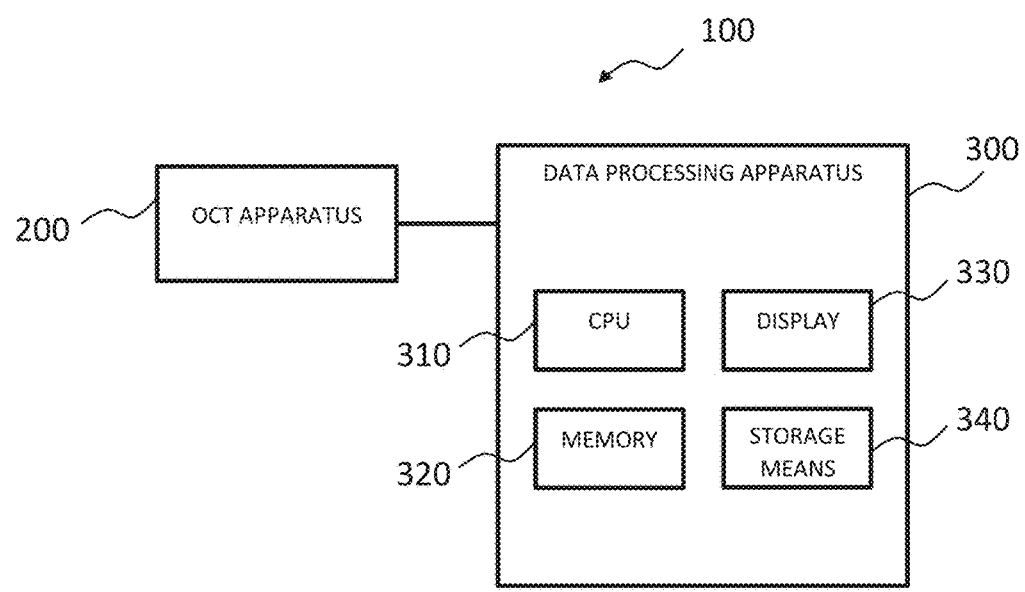
FIG. 16 is a block diagram of an apparatus for calculating OCTA angiograms with eye bulk motions compensation according to a fourth embodiment.

As shown in FIG. 16 the system (apparatus) 100 for calculating the OCTA angiograms while compensating for eye motions during OCTA measurement includes an OCT apparatus 200 and a data processing apparatus 300.

The OCT apparatus 200 may be any suitable OCT apparatus, for example that discussed in non-patent literature 3.

The data processing apparatus includes a CPU 310, a memory 320, a display 330 and a storage means 340. The storage means 340 stores programs that may be loaded into the memory 320 and executed by the CPU 310. In particular the programs executed by the CPU 310 perform the processes discussed in any of the first to third embodiments. Thus the CPU 310, and so the data processing apparatus 300, is arranged to perform the processes of the first, second or third embodiments. Furthermore, the CPU 310, and so the data processing apparatus 300, may be arranged to be able to perform all of the processes of the first, second or third embodiments. In this later case, a user may simply select which one of the first, second and third embodiment processes is used.

The memory 320 is used by the CPU 310 as a work memory. The results of the processes and calculations by the CPU 310 may be displayed on the display 330. For example, the resultant OCTA map may be displayed on the display 330. Furthermore the results of the calculations by the CPU 310, e.g. the OCTA map, may be stored in the storage means 340. A number of results, or OCTA maps, may be stored in the storage means 340 for a number of different patients.

Although, FIG. 16 shows the system 100 as having the OCT apparatus 200 and the data processing apparatus 300 as separate units, they may be contained in a single unit or apparatus.

Other Embodiments

The above described methods are applied to generating an OCTA image, however the above described methods can be also applied to generating an averaged image. The averaged image (e.g. an averaged B-scan image) is generated based on a plurality of B-scans within the B-scan set. The plurality of B-scans are averaged after the plurality of B-scans are aligned using a first alignment process and a second alignment process.

The present invention can also be implemented through processing in which a program that implements one or more functions of the any of the above embodiments described above is supplied to a system or an apparatus via a network or in the form of a storage medium and one or more processors in the system or the apparatus read out and execute the program. In addition, the embodiments can also be implemented by a circuit (e.g., application specific integrated circuit (ASIC)) that implements one or more functions.

While the present invention has been described with reference to embodiments, it is to be understood that the invention is not limited to the disclosed embodiments.

In other words, the present invention can be implemented in various forms without departing from the principal features of the present invention.

The scope of the following claims is to be accorded the broadest interpretation so as to encompass all such modifications and equivalent structures and functions.

The invention claimed is:

1. A method for compensating for motion artefacts in Optical Coherence Tomography, the method comprising:
   acquiring a B-scan set including a plurality of B-scan OCT images acquired at least a position corresponding to a target position of a fundus of an eye; and
   aligning the plurality of B-scans within the B-scan set using a first alignment process and a second alignment process, wherein the second alignment process is performed on the B-scan images within the B-scan set aligned by the first alignment process;
   wherein the first alignment process aligns the B-scan images within the B-scan set at a first resolution in at least an axial direction, and the second alignment process aligns the B-scan images within the B-scan set aligned in the first alignment process at a second resolution being a higher resolution than the first resolution in at least the axial direction.

2. The method according to claim 1, wherein an alignment range of the second alignment process is smaller than an alignment range of the first alignment process.

3. The method according to claim 1, wherein;
   the first alignment process and the second alignment process are also performed in the horizontal direction of the B-scan images.

4. The method according claim 1, wherein the second alignment process is performed to obtain a shift value in the second resolution to align B-scan images within the B-scan set.

5. The method according to claim 4, wherein the shift value is calculated by using average decorrelation values calculated between B-scan images within the B-scan set.

6. The method according to claim 1, wherein the second alignment process includes determining for B-scans within the B-scan set, a shift amount, and applying the shift amount to a second B-scan within the B-scan set, so that the second B-scan within the B-scan set is shifted such that the second B-scan is matched with a first B-scan within the B-scan set.

7. The method according to claim 1, wherein each of the B-scan images is divided into a plurality of portions, and the second alignment process is performed on each corresponding portion of B-scans within the B-scan set.

8. The method according to claim 7, wherein the second alignment process includes determining a shift amount between the corresponding portions of B-scans within the B-scan set, and applying the shift amount to the corresponding portion of a second B-scan within the B-scan set, so that the corresponding portion of the second B-scan within the B-scan set is shifted such that the corresponding portion of the second B-scan is matched with the corresponding portion of a first B-scan within the B-scan set.

9. The method according to claim 1, further comprising;
   determining retinal layers of the fundus in the B-scan images, wherein;

the second alignment process is performed based on the determined retinal layers.

10. The method according to claim 9, wherein the determined retinal layers include at least one of the boundary of the Vitreous body and the Inner Limiting Membrane, and the boundary of the Retinal Pigmented Epithelium of the fundus.

11. The method according to claim 1, further comprising; calculating an OCT angiogram from the aligned B-scans within the B-scan set, wherein the OCT angiogram is a motion contrast data set related to blood flow information.

12. A system for compensating for motion artefacts in Optical Coherence Tomography comprising:
an OCT apparatus for obtaining a plurality of B-scan sets including a plurality of B-scan OCT images acquired at least a position corresponding to a target position of a fundus of an eye; and
a data processing apparatus for performing the method according to claim 1 to generate an angiogram of the fundus.

13. A non-transitory computer readable storage medium storing a program for causing a computer to execute a method for compensating for motion artefacts in Optical Coherence Tomography, the method comprising:
acquiring a B-scan set including a plurality of B-scan OCT images acquired at least a position corresponding to a target position of a fundus of an eye; and
aligning the plurality of B-scans within the B-scan set using a first alignment process and a second alignment process, wherein the second alignment process is performed on the B-scan images within the B-scan set aligned by the first alignment process;
wherein the first alignment process aligns the B-scan images within the B-scan set at a first resolution in at least an axial direction, and the second alignment process aligns the B-scan images within the B-scan set aligned in the first alignment process at a second resolution being a higher resolution than the first resolution in at least the axial direction.

* * * * *